US012616537B2

(12) United States Patent
Wang et al.

(10) Patent No.: US 12,616,537 B2
(45) Date of Patent: May 5, 2026

(54) CONTROL METHOD FOR ARTHROPLASTY SURGICAL ROBOT

(71) Applicant: SHANDONG HANGWEI ORTHOPEDICS MEDICAL INSTRUMENT CO., LTD., Weifang (CN)

(72) Inventors: Kunzheng Wang, Weifang (CN); Shuo Sun, Weifang (CN); Jianran Wang, Weifang (CN); Dexiu Sun, Weifang (CN); Shaobin Hao, Weifang (CN); Delu Wang, Weifang (CN); Hui Dong, Weifang (CN)

(73) Assignee: SHANDONG HANGWEI ORTHOPEDICS MEDICAL INSTRUMENT CO., LTD., Weifang (CN)

( * ) Notice: Subject to any disclaimer, the term of this patent is extended or adjusted under 35 U.S.C. 154(b) by 88 days.

(21) Appl. No.: 18/709,900

(22) PCT Filed: Nov. 4, 2022

(86) PCT No.: PCT/CN2022/129716
§ 371 (c)(1),
(2) Date: May 14, 2024

(87) PCT Pub. No.: WO2023/116232
PCT Pub. Date: Jun. 29, 2023

(65) Prior Publication Data
US 2025/0000594 A1     Jan. 2, 2025

(30) Foreign Application Priority Data
Dec. 25, 2021    (CN) .......................... 202111605189.3

(51) Int. Cl.
*A61B 34/32*      (2016.01)
*A61B 17/17*      (2006.01)
*A61B 17/56*      (2006.01)
*A61B 34/10*      (2016.01)

(52) U.S. Cl.
CPC .......... *A61B 34/32* (2016.02); *A61B 17/1764* (2013.01); *A61B 2017/564* (2013.01); *A61B 2034/102* (2016.02); *A61B 2034/105* (2016.02)

(58) Field of Classification Search
CPC ... A61B 34/32; A61B 17/1764; A61B 17/809; A61B 17/1695
See application file for complete search history.

(56) References Cited

U.S. PATENT DOCUMENTS

| | | | | |
|---|---|---|---|---|
| 6,033,415 A | * | 3/2000 | Mittelstadt | ................ G06T 3/02 600/425 |
| 6,322,567 B1 | * | 11/2001 | Mittelstadt | ............. A61B 34/70 606/130 |
| 2010/0256479 A1 | | 10/2010 | Park et al. | |

FOREIGN PATENT DOCUMENTS

| | | |
|---|---|---|
| CN | 103584932 A | 2/2014 |
| CN | 103860293 A | 6/2014 |
| CN | 107088091 A | 8/2017 |
| CN | 109925055 A | 6/2019 |
| CN | 110613469 A | 12/2019 |
| CN | 111166538 A | 5/2020 |
| CN | 113616273 A | 11/2021 |
| CN | 114305697 A | 4/2022 |

OTHER PUBLICATIONS

Jan. 28, 2023 International Search Report issued in International Patent Application No. PCT/CN2022/129716.
Jan. 28, 2023 Written Opinion issued in International Patent Application No. PCT/CN2022/129716.

* cited by examiner

*Primary Examiner* — Andrew Yang
(74) *Attorney, Agent, or Firm* — Oliff PLC

(57) ABSTRACT

A control method for an arthroplasty surgical robot includes: capturing a bone image, transmitting the image to a computer system, and acquiring image data of a bone; selecting a suitable prosthesis model and placing it on a diseased joint for matching, wherein the overlapping part between the model and the bone is the part that needs to be removed and replaced; mounting signal sources; capturing a bone image again, including the signal sources and the joint part; establishing a coordinate system using the signal sources as the origin, and calculating and memorizing an interface between the model and the bone overlapping part and the coordinates of the interface in the coordinate system; and receiving the coordinates by a surgical robot, and obtaining the positional coordinates by the surgical robot of a part of the diseased joint that needs to be removed, and performing a surgical operation by the surgical robot.

8 Claims, No Drawings

CONTROL METHOD FOR ARTHROPLASTY SURGICAL ROBOT

TECHNICAL FIELD

The invention relates to a control method of a joint arthroplasty surgical robot and belongs to the technical field of electronic control.

BACKGROUND

Presently, surgical precision, minimally invasive approaches, and intelligent safety represent the focal objectives for surgeons. With the advancements in Computer Aided Surgery (CAS), Computer Aided Minimally Invasive Surgery (CAMIS), Computer Aided Orthopedics Surgery (CAOS), and their interdisciplinary integration, surgical navigation robots have become one of the main development directions for future surgical procedures. These surgical navigation robots involve multiple technologies such as automation, artificial intelligence, electronic information, and medical image processing, seamlessly integrating principles of surgery with computer software and construction machinery. They extend the visual and tactile capabilities of surgeons, enhancing the precision, safety, and reproducibility of surgical procedures, thereby assisting in the completion of high-risk complex surgeries previously deemed unattainable and effectively reducing surgical trauma.

For example, patent No. "201910164262.4" discloses a pre-positioning method of a prosthesis before a joint arthroplasty surgery, which includes the following steps: acquiring CT image data; performing segmentation and three-dimensional reconstruction on a bone of a patient in the CT image data to obtain a bone model of the patient in a model space, wherein the bone model includes a joint three-dimensional model; selecting at least two fixed feature points on the end face of the joint three-dimensional model; selecting the same number of fixed points at the same position as the fixed feature points of the joint three-dimensional model on the end face of the prosthesis model; performing three-dimensional matching on the joint three-dimensional model and the prosthesis model, realizes the pre-positioning of the prosthesis, thereby the efficiency and the precision of pre-positioning are improved.

SUMMARY OF THE INVENTION

In view of the above problem, the invention provides a control method for a joint arthroplasty surgical robot, which can accurately determine a diseased joint section through three-dimensional modeling and a coordinate system establishment mode. As a result, the surgical robot can perform accurate operations with a high degree of precision, ensuring a high matching rate between the prosthesis and the original diseased joint. This significantly enhances the accuracy of the surgery.

In order to solve the above technical problems, the invention adopts the following technical scheme:

A control method for an arthroplasty surgical robot, which comprises the following steps:

a first step of capturing a bone image of a patient, transmitting the bone image to a computer system, and acquiring image data of a bone by the computer system;

a second step of placing the bone image according to a normal biological force line in the computer system;

a third step of selecting, in the computer system, a suitable prosthesis model and placing the prosthesis model on a diseased joint for matching, wherein after matching is completed, the overlapping part between the joint prosthesis model and the bone is the part that needs to be removed and replaced;

a fourth step of selecting one or more fixed points arbitrarily on a tibia and a femur of the diseased joint respectively after the patient arrives on an operating table, fixing a bracket at the fixed points through bone screws, equipping each bracket with at least three signal sources not aligned in the same straight line, serving as signal sending ends;

a fifth step of capturing a bone image of the patient again, wherein the photographing range comprises the signal sources and the joint parts, transmitting the bone image to the computer system;

a sixth step of establishing a coordinate system by taking the positions of the signal sources on the tibia and femur as the origin in the computer system, and correspondingly placing the bone image obtained in the fifth step onto the matched joint prosthesis model bone image in the third step in the coordinate system in an overlapping way;

and the computer system automatically calculates and memorizes an interface between the joint prosthesis model and the tibia bone and the femur bone overlapping part obtained in the sixth step and the coordinates of the interface in the coordinate system, and outputs the coordinates to the surgical robot;

a seventh step of receiving the coordinates by a surgical robot, and obtaining, in conjunction with received signals which are sent by the signal sources, the positional coordinates by the surgical robot, in the coordinate system, of a part of the diseased joint that needs to be removed, and performing osteotomy resection by the surgical robot based on the positional coordinates, completing the placement of the joint prosthesis.

Furthermore, in the sixth step, the positions of the signal sources on the tibia and the femur are used as the origin to respectively establish a tibia coordinate system and a femur coordinate system, and the computer system automatically calculates and memorizes the coordinates of the interface in the tibia coordinate system and the femur coordinate system respectively.

Furthermore, in the first step, the bone image of the patient is shot through X-ray, the bone of the patient is aligned according to an anteroposterior full-length position and a lateral position, the lateral position is vertical to the anteroposterior position, and an anteroposterior X-ray film and a lateral X-ray film of the full length of the bone are taken.

Furthermore, in the fifth step, capturing the bone image of the patient again, and the bone direction determined in the first step is used for shooting an anteroposterior X-ray film and a lateral X-ray film of the bone of the patient, and the photographing range comprises the signal sources and the joint parts.

Furthermore, in the sixth step, within the computer system and the X-ray image data containing the signal sources shot in the fifth step, the X-ray image containing the signal sources shot in the fifth step and the full-length X-ray images of the matched joint prosthesis model in the third step are placed correspondingly in an overlapping way in the tibia coordinate system and the femur coordinate system respectively.

Furthermore, in the first step, capturing a bone image of a patient via CT imaging. In the fifth step, capturing the bone image of the patient again via CT imaging, and the photographing range comprises the signal sources and the joint parts.

Furthermore, in the second step, within the computer system, the three-dimensional modeling is performed according to the CT images, and the bone of the patient is placed according to the normal biological force line to obtain a first bone three-dimensional model in the computer system. The first bone three-dimensional model includes the joint parts.

Furthermore, in the sixth step, within the computer system, three-dimensional modeling is performed on the CT images containing the signal sources and joint parts, resulting in a second bone three-dimensional model, which is placed correspondingly in an overlapping way with the first bone three-dimensional model matched of the joint prosthesis model in the third step in the tibial coordinate system and the femoral coordinate system respectively.

Furthermore, the method comprises the following steps:
a first step of aligning the bone of the patient according to the anteroposterior full-length position and the lateral position, the lateral position is perpendicular to the anteroposterior position, shooting an anteroposterior X-ray film and a lateral X-ray film of the full length of the bone, uploading the X-ray films to a computer system, and obtaining the image data of the X-ray films by the computer system;
a second step of placing the anteroposterior X-ray film and the lateral X-ray film according to a normal biological force line in the computer system respectively;
a third step of selecting, in the computer system, a suitable joint prosthesis model preset in the computer system by a surgeon, and placing the joint prosthesis model on a diseased joint, and matching the joint prosthesis model with the bone in the X-ray film in an anteroposterior position and a lateral position by the surgeon according to experience;
within computer system, after the joint prosthesis model and the bone are matched, the overlapping part between the joint prosthesis model and the bone is the part that needs to be removed and replaced;
a fourth step of selecting one or more fixed points arbitrarily on a tibia and a femur of the diseased joint respectively after the patient arrives on the operating table, fixing a bracket at the fixed points through bone screws, equipping each bracket with at least three signal sources not aligned in the same straight line, serving as signal sending ends;
a fifth step of following the directions of bone determined in the first step, an anteroposterior X-ray image and a lateral X-ray image of the patient's bone are shot again, the photographing range comprises the signal sources and the joint parts, uploading the bone images to the computer system;
a sixth step of establishing, in the computer system, a tibia coordinate system and a femur coordinate system respectively by taking the position of the signal source on the tibia and femur as the origin in the X-ray image data containing the signal sources shot in the fifth step, the X-ray images containing the signal sources shot in the fifth step and the full-length X-ray images of the matched joint prosthetic model in the third step are placed correspondingly in an overlapping way in the tibia coordinate system and the femur coordinate system respectively;
and the computer system automatically calculates and memorizes an interface between the joint prosthesis model and the tibia bone and the femur bone overlapping part obtained in the sixth step and the coordinates of the interface in the tibia coordinate system and the femur coordinate system respectively, and outputs the coordinates to the surgical robot;
a seventh step of equipping with a signal receiving end on the surgical robot to receive signals from the signal sources, receiving the coordinates by a surgical robot, and obtaining, in conjunction with received signals which are sent by the signal sources, the positional coordinates by the surgical robot, in the coordinate system, of a part of the diseased joint that needs to be removed, at this point, exposing the bone by the surgeon, and performing osteotomy resection by the surgical robot based on the positional coordinates, after the resection, placing prostheses of the same size as the prosthesis models onto the joint by the surgeon, completing the placement of the joint prosthesis.

Furthermore, the method comprises the following steps:
a first step of shooting a CT image of the bone of a patient, uploading the shot CT images to a computer system, and acquiring image data of the CT image by the computer system;
a second step of performing bone three-dimensional modeling on the CT image in the computer system, and placing the bone of a patient according to a normal biological force line to obtain a first bone three-dimensional model of the bone in the computer system, resulting in the first three-dimensional bone model, including the joint part;
a third step of selecting, in the computer system, a suitable joint prosthesis model preset in the computer system by a surgeon, and placing the joint prosthesis model on a diseased joint, and matching the joint prosthesis model with the bone in the first bone three-dimensional model by the surgeon according to experience;
within computer system, after the joint prosthesis model and the bone are matched, the overlapping part between the joint prosthesis model and the bone is the part that needs to be removed and replaced;
a fourth step of selecting one or more fixed points arbitrarily on a tibia and a femur of the diseased joint respectively after the patient arrives on the operating table, fixing a bracket at the fixed points through bone screws, equipping each bracket with at least three signal sources not aligned in the same straight line, serving as signal sending ends;
a fifth step of capturing a CT image of the bone of the patient again, the photographing range comprises the signal sources and the joint parts, uploading the CT image to the computer system;
a sixth step of performing three-dimensional modeling on the CT images containing the signal sources and joint parts in the computer system, resulting in a second bone three-dimensional model, establishing a tibia coordinate system and a femur coordinate system respectively by taking the position of the signal source on the tibia and femur as the origin, placing correspondingly in an overlapping way with the first bone three-dimensional model matched of the joint prosthesis model in the third step in the tibial coordinate system and the femoral coordinate system respectively;
and the computer system automatically calculates and memorizes an interface between the joint prosthesis model and the tibia bone and the femur bone model overlapping part obtained in the sixth step and the coordinates of the interface in the tibia coordinate system and the femur coordinate system respectively, and outputs the coordinates to the surgical robot;

a seventh step of equipping with a signal receiving end on the surgical robot to receive signals from the signal sources, receiving the coordinates by a surgical robot, and obtaining, in conjunction with received signals which are sent by the signal sources, the positional coordinates by the surgical robot, in the coordinate system, of a part of the diseased joint that needs to be removed, at this point, exposing the bone by the surgeon, and performing osteotomy resection by the surgical robot based on the positional coordinates, after the resection, placing prostheses of the same size as the prosthesis models onto the joint by the surgeon, completing the placement of the joint prosthesis.

Compared with the prior art, by adopting the technical scheme aforementioned, the invention has the following technical effects:

1. compared with the Chinese patent No. "201910164262.4" in the background art, the present invention determines fixed points on the patient's bone, using signal sources installed on the fixed points as feature points, while the Chinese patent No. "201910164262.4" selects fixed feature points on the joint's three-dimensional model and prosthesis model;

2. The Chinese patent No. "201910164262.4", does not allow for arbitrary selection of fixed feature points on the joint's three-dimensional model and prosthetic model, requiring point clouds of at least two fixed feature points for initial registration, whereas the present invention allows for arbitrary selection of fixed feature points, with a quantity equal to or greater than one being sufficient, simplifying the selection process;

3. The purpose of selecting the fixed feature points on the joint three-dimensional model and the prosthesis model in the Chinese patent No. "201910164262.4" is to align the prosthesis with the osteotomy resection location on the joint, while in the present invention, selecting fixed feature points serves to fix the bracket, with signal sources fixed on the bracket, used to establish a coordinate system and monitor the real-time position of the patient's bone;

4. In the Chinese patent No. "201910164262.4", fixed feature points need to be selected and registered twice on the joint three-dimensional model and prosthesis model to precisely match the point clouds of the fixed feature points, achieving prosthesis placement at the osteotomy resection location. In contrast, in the present invention, based on the surgeon's experience, the joint prosthesis model is directly placed at the diseased bone in the computer system, the overlapping part between the joint prosthesis model and the bone is the part that needs to be removed and replaced, so that the surface that needs to be removed can be accurately determined, which is convenient for subsequent surgical operation.

5. In the Chinese patent No. "201910164262.4", it determines the pre-positioning of the prosthesis at the osteotomy resection location through point clouds matching, requiring multiple matching attempts and fine-tuning, the present invention establishes a coordinate system to determine the coordinate position of the surface that needs to be removed, achieving precise and accurate positioning without the need for multiple matching attempts.

6. In the present invention, the position where the diseased joint needs to be removed is accurately deter-mined within the coordinate system, ensuring high accuracy and efficiency in positioning.

DETAILED DESCRIPTION OF THE EMBODIMENT

Embodiment 1

A control method for an arthroplasty surgical robot, which comprises the following steps:

a first step of aligning the bone of the patient according to the anteroposterior full-length position and the lateral position, the lateral position is perpendicular to the anteroposterior position, shotting an anteroposterior X-ray film and a lateral X-ray film of the full length of the bone, uploading the X-ray films to a computer system, and obtaining the image data of the X-ray films by the computer system;

a second step of placing the anteroposterior X-ray film and the lateral X-ray film according to a normal bio-logical force line in the computer system respectively;

a third step of selecting, in the computer system, a suitable joint prosthesis model preset in the computer system by a surgeon, and placing the joint prosthesis model on a diseased joint, and matching the joint prosthesis model with the bone in the X-ray film in an anteroposterior position and a lateral position by the surgeon according to experience;

within computer system, after the joint prosthesis model and the bone are matched, the overlapping part between the joint prosthesis model and the bone is the part that needs to be removed and replaced;

a fourth step of selecting one or more fixed points arbitrarily on a tibia and a femur of the diseased joint respectively after the patient arrives on the operating table, fixing a bracket at the fixed points through bone screws, equipping each bracket with at least three signal sources not aligned in the same straight line, serving as signal sending ends;

a fifth step of subsequently, following the directions of bone determined in the first step, an anteroposterior X-ray image and a lateral X-ray image of the patient's bone are shot again, the photographing range comprises the signal sources and the joint parts, uploading the bone images to the computer system;

a sixth step of establishing, in the computer system, a tibia coordinate system and a femur coordinate system respectively by taking the position of the signal source on the tibia and femur as the origin in the X-ray image data containing the signal sources shot in the fifth step, the X-ray images containing the signal sources shot in the fifth step and the full-length X-ray images of the matched joint prosthetic model in the third step are placed correspondingly in an overlapping way in the tibia coordinate system and the femur coordinate system respectively;

and the computer system automatically calculates and memorizes an interface between the joint prosthesis model and the tibia bone and the femur bone overlapping part obtained in the sixth step and the coordinates of the interface in the tibia coordinate system and the femur coordinate system respectively, and outputs the coordinates to the surgical robot;

a seventh step of equipping with a signal receiving end on the surgical robot to receive signals from the signal sources, receiving the coordinates by a surgical robot, and obtaining, in conjunction with received signals which are sent by the signal sources, the positional coordinates by the surgical robot, in the coordinate system, of a part of the diseased joint that needs to be removed, at this point, exposing the bone by the surgeon, and performing osteotomy resection by the surgical robot based on the positional coordinates, after the resection, placing prostheses of the same size as the prosthesis models onto the joint by the surgeon, completing the placement of the joint prosthesis.

When placing joint, the scaling ratio of preoperative X-ray film and human body should be the same as that during operation, and the surgical robot automatically calculates the coordinates of the actual bone.

Embodiment 2

A first step of shooting a CT image of the bone of a patient, uploading the shot CT images to a computer system, and acquiring image data of the CT image by the computer system;

a second step of performing bone three-dimensional modeling on the CT image in the computer system, and placing the bone of a patient according to a normal biological force line to obtain a first bone three-dimensional model of the bone in the computer system, resulting in the first three-dimensional bone model, including the joint part;

a third step of selecting, in the computer system, a suitable joint prosthesis model preset in the computer system by a surgeon, and placing the joint prosthesis model on a diseased joint, and matching the joint prosthesis model with the bone in the first bone three-dimensional model by the surgeon according to experience;

within computer system, after the joint prosthesis model and the bone are matched, the overlapping part between the joint prosthesis model and the bone is the part that needs to be removed and replaced;

a fourth step of selecting one or more fixed points arbitrarily on a tibia and a femur of the diseased joint respectively after the patient arrives on the operating table, fixing a bracket at the fixed points through bone screws, equipping each bracket with at least three signal sources not aligned in the same straight line, serving as signal sending ends;

a fifth step of capturing a CT image of the bone of the patient again, the photographing range comprises the signal sources and the joint parts, uploading the CT image to the computer system;

a sixth step of performing three-dimensional modeling is performed on the CT images containing the signal sources and joint parts in the computer system, resulting in a second bone three-dimensional model, establishing a tibia coordinate system and a femur coordinate system respectively by taking the position of the signal source on the tibia and femur as the origin, placing correspondingly in an overlapping way with the first bone three-dimensional model matched of the joint prosthesis model in the third step in the tibial coordinate system and the femoral coordinate system respectively;

and the computer system automatically calculates and memorizes an interface between the joint prosthesis model and the tibia bone and the femur bone model overlapping part obtained in the sixth step and the coordinates of the interface in the tibia coordinate system and the femur coordinate system respectively, and outputs the coordinates to the surgical robot;

a seventh step of equipping with a signal receiving end on the surgical robot to receive signals from the signal sources, receiving the coordinates by a surgical robot, and obtaining, in conjunction with received signals which are sent by the signal sources, the positional coordinates by the surgical robot, in the coordinate system, of a part of the diseased joint that needs to be removed, at this point, exposing the bone by the surgeon, and performing osteotomy resection by the surgical robot based on the positional coordinates, after the resection, placing prostheses of the same size as the prosthesis models onto the joint by the surgeon, completing the placement of the joint prosthesis.

The surgical robot is connected with the computer system which has the functions of three-dimensional modeling and coordinate system generation.

The description of the present invention is provided for the purpose of illustration and description and is not intended to be exhaustive or to limit the invention to the precise forms disclosed. Many modifications and variations will be apparent to those skilled in the art. The choice and description of embodiments are made to better illustrate the principles of the invention and its practical applications, enabling those skilled in the art to understand the invention and design various embodiments with various modifications suitable for specific purposes.

The invention claimed is:

1. A control method for an arthroplasty surgical robot, the method comprising:

a first step of capturing a bone image of a patient, transmitting the bone image to a computer system, and acquiring image data of a bone by the computer system;

a second step of placing the bone image according to a normal biological force line in the computer system;

a third step of selecting, in the computer system, a suitable prosthesis model and placing the prosthesis model on a diseased joint for matching, wherein after matching is completed, the overlapping part between the joint prosthesis model and the bone is the part that needs to be removed and replaced;

a fourth step of selecting one or more fixed points arbitrarily on a tibia and a femur of the diseased joint respectively after the patient arrives on an operating table, fixing a bracket at the fixed points through bone screws, equipping each bracket with at least three signal sources not aligned in the same straight line, serving as signal sending ends;

a fifth step of capturing a bone image of the patient again, wherein a photographing range comprises the signal sources and the joint parts, transmitting the bone image to the computer system;

a sixth step of establishing a coordinate system by taking the positions of the signal sources on the tibia and femur as the origin in the computer system, and correspondingly placing the bone image obtained in the fifth step onto the matched joint prosthesis model bone image in the third step in the coordinate system in an overlapping way; and the computer system automatically calculates and memorizes an interface between the joint prosthesis model and the tibia bone and the femur bone overlapping part obtained in the sixth step and the coordinates of the interface in the coordinate system, and outputs the coordinates to the surgical robot;

a seventh step of receiving the coordinates by a surgical robot, and obtaining, in conjunction with received signals which are sent by the signal sources, the positional coordinates by the surgical robot, in the coordinate system, of a part of the diseased joint that needs to be removed, and performing osteotomy resection by the surgical robot based on the positional coordinates, completing the placement of the joint prosthesis.

2. The control method for the arthroplasty surgical robot according to claim 1, wherein in the sixth step, the positions of the signal sources on the tibia and the femur are used as the origin to respectively establish a tibia coordinate system and a femur coordinate system, and the computer system automatically calculates and memorizes the coordinates of the interface in the tibia coordinate system and the femur coordinate system respectively.

3. The control method for the arthroplasty surgical robot according to claim 2, wherein in the first step, the bone image of the patient is shot through X-ray, the bone of the patient is aligned according to an anteroposterior full-length position and a lateral position, the lateral position is vertical to the anteroposterior position, and an anteroposterior X-ray film and a lateral X-ray film of the full length of the bone are taken.

4. The control method for the arthroplasty surgical robot according to claim 3, wherein in the fifth step, capturing a bone image of the patient again, and the bone direction determined in the first step is used for shooting an anteroposterior X-ray film and a lateral X-ray film of the bone of the patient, and the photographing range comprises the signal sources and the joint parts.

5. The control method for the arthroplasty surgical robot according to claim 4, wherein in the sixth step, within the computer system and the X-ray image data containing the signal sources shot in the fifth step, the X-ray image containing the signal sources shot in the fifth step and the full-length X-ray images of the matched joint prosthesis model from the third step are placed correspondingly in an overlapping way in the tibia coordinate system and the femur coordinate system respectively.

6. The control method for the arthroplasty surgical robot according to claim 2, wherein in the first step, capturing a bone image of a patient via CT imaging, in the fifth step, capturing the bone image of the patient again via CT imaging, and the photographing range comprises the signal sources and the joint parts.

7. The control method for the arthroplasty surgical robot according to claim 6, wherein in the second step, within the computer system, a three-dimensional modeling is performed according to the CT images, and the bone of the patient is placed according to the normal biological force line to obtain a first bone three-dimensional model in the computer system, the first bone three-dimensional model includes the joint parts.

8. The control method for the arthroplasty surgical robot according to claim 7, wherein in the sixth step, within the computer system, a three-dimensional modeling is performed on the CT images containing the signal sources and joint parts, resulting in a second bone three-dimensional model, which is placed correspondingly in an overlapping way with the first bone three-dimensional model matched of the joint prosthesis model in the third step in the tibial coordinate system and the femoral coordinate system respectively.

* * * * *